US007625188B2

(12) United States Patent
Dow (10) Patent No.: US 7,625,188 B2
(45) Date of Patent: Dec. 1, 2009

(54) HEART BOOSTER PUMP (76) Inventor: Glendal R. Dow, 1320 Hardisty, Bedford, TX (US) 76021

( * ) Notice: Subject to any disclaimer, the term of this patent is extended or adjusted under 35 U.S.C. 154(b) by 244 days.

(21) Appl. No.: 11/750,109

(22) Filed: May 17, 2007

(65) Prior Publication Data
US 2007/0266847 A1 Nov. 22, 2007

Related U.S. Application Data (60) Provisional application No. 60/801,010, filed on May 17, 2006.

(51) Int. Cl.
F04B 49/00 (2006.01)

(52) U.S. Cl. .................. 417/223; 417/212; 92/140; 74/25; 604/152

(58) Field of Classification Search ............. 417/223, 417/374, 15, 212, 218; 92/140; 74/25; 604/152, 604/153
See application file for complete search history.

(56) References Cited

U.S. PATENT DOCUMENTS

| | | | |
|---|---|---|---|
| 1,553,009 A | 9/1925 | Stuke | |
| 3,026,859 A * | 3/1962 | Eugene et al. | 123/39 |
| 4,595,495 A * | 6/1986 | Yotam et al. | 210/101 |
| 4,860,702 A | 8/1989 | Doundoulakis | |
| 4,897,189 A | 1/1990 | Greenwood et al. | |
| 5,151,015 A * | 9/1992 | Bauer et al. | 417/415 |
| 5,492,050 A * | 2/1996 | Holtgraver | 92/74 |
| 5,908,014 A | 6/1999 | Leithinger | |
| 6,164,924 A * | 12/2000 | Gruett et al. | 417/222.1 |
| 6,224,347 B1 | 5/2001 | Clark et al. | |
| 6,349,684 B1 | 2/2002 | deGooijer | |
| 6,408,814 B2 | 6/2002 | Shigemori | |
| 6,564,762 B2 | 5/2003 | Dow | |
| 6,729,853 B2 | 5/2004 | Umemura et al. | |
| 6,948,460 B1 | 9/2005 | Dow | |
| 7,011,052 B2 | 3/2006 | Dow | |

* cited by examiner

Primary Examiner—Devon C Kramer
Assistant Examiner—Todd D Jacobs
(74) Attorney, Agent, or Firm—Bracewell & Giuliani LLP (57) ABSTRACT A heart pump has a pump chamber and a pump element that strokes between a retracted and an extended position. A motor rotates a drive shaft in a single direction. A reversing mechanism coupled between the drive shaft of the motor and the pump element converts rotary motion of the drive shaft to reciprocal stroking movement of the pump element. A mechanical stroke length controller connected to the reversing mechanism varies the stroke length in response to changes in fluid pressure in the pump chamber.

17 Claims, 6 Drawing Sheets

HEART BOOSTER PUMP

CROSS-REFERENCE TO RELATED APPLICATION

This application claims priority to provisional application 60/801,010, filed May 17, 2006.

FIELD OF THE INVENTION

This invention relates in general to pumps and in particular to a driver mechanism for a heart booster pump.

BACKGROUND OF THE INVENTION

Mechanical heart pumps are typically external devices temporarily used when a patient is undergoing surgery to repair the heart or to transplant another heart. Mechanical pumps to be implanted are also known but not in extensive use because of the technical problems to be solved. If used for an extended time, the pump ideally should duplicate the human heart. The human heart has a pulse and operates at different blood pressure levels depending upon the type of exertion of the patient. A patient's arteries and veins will naturally expand during exertion, which tends to lower the blood pressure. The patient's arteries and veins will contract while the patient is sedentary, increasing the blood pressure back to an at rest level. Also, while the patient is exercising, in addition to the pulse rate being higher, each stroke of the human heart will pump more blood than while the patient is sedentary.

Rotary heart pumps cannot duplicate a pulse. While reciprocating heart pumps are known, they normally are configured to pump the same volume of blood with each stroke. While workable, changes in blood pressure caused by exertion of the patient are detrimental to the check valves and other components of the pump chamber if the same volume of fluid is pumped with each stroke. Consequently, known reciprocating type heart pumps must be replaced at fairly frequent intervals.

SUMMARY

The pump of this invention has a pump element that strokes between retracted and extended positions to pump fluid from a chamber. A reversing mechanism is coupled between a drive shaft of a motor and the pump element for converting rotary motion of the drive shaft in a single direction to reciprocal stroking movement of the pump element. A mechanical stroke length controller is incorporated in the reversing mechanism for varying a stroke length of the pump element in response to changes in fluid pressure in the pump chamber.

In the preferred embodiment, the rate at which the pump element moves toward the retracted position is proportional to the fluid pressure within the chamber. Also, the point at which the reversing mechanism changes from an extension mode to a retraction mode is dependent upon the fluid pressure within the chamber. The stroke length controller has a spring assembly that biases the reversing mechanism into the extension mode. If the fluid pressure in the chamber exceeds the bias force created by the spring assembly, the stroke controller causes the reversing mechanism to shift to the retraction mode. Preferably, the stroke length controller causes the retraction mode to occur more quickly than the extension mode.

In the preferred embodiment, the reversing mechanism comprises a cam that rotates relative to the housing an increment of one turn in a first direction while the reversing mechanism is in the extension mode and an increment of one turn in a second direction while the reversing mechanism is in the retraction mode. The cam engages a cam follower carried with the pump element assembly. As the reversing mechanism rotates the cam in a first direction, the cam pushes the cam follower and the pump element toward the extended position. As the reversing mechanism rotates the cam in a second direction, the cam allows the pump element to retract. The cam has an extension end stop that engages the cam follower when the pump element is at a fully extended position and a retraction end stop that engages the cam follower when the pump element is at a fully retracted position. The reversing mechanism rotates the cam in the second direction when the extension end stop contacts the cam follower and rotates the cam in the first direction when the retraction end stop contacts the cam follower.

If the fluid pressure in the chamber is above a selected level and the reversing mechanism in the extension mode, the stroke length controller will cause the reversing mechanism to rotate the cam in the second direction prior to the extension end stop contacting the cam follower. If the fluid pressure in the chamber is below a selected level during the retraction stroke, the reversing mechanism causes the cam to begin rotating in the first direction before the pump element reaches the fully retracted position.

DETAILED DESCRIPTION OF THE INVENTION

Figure 1:
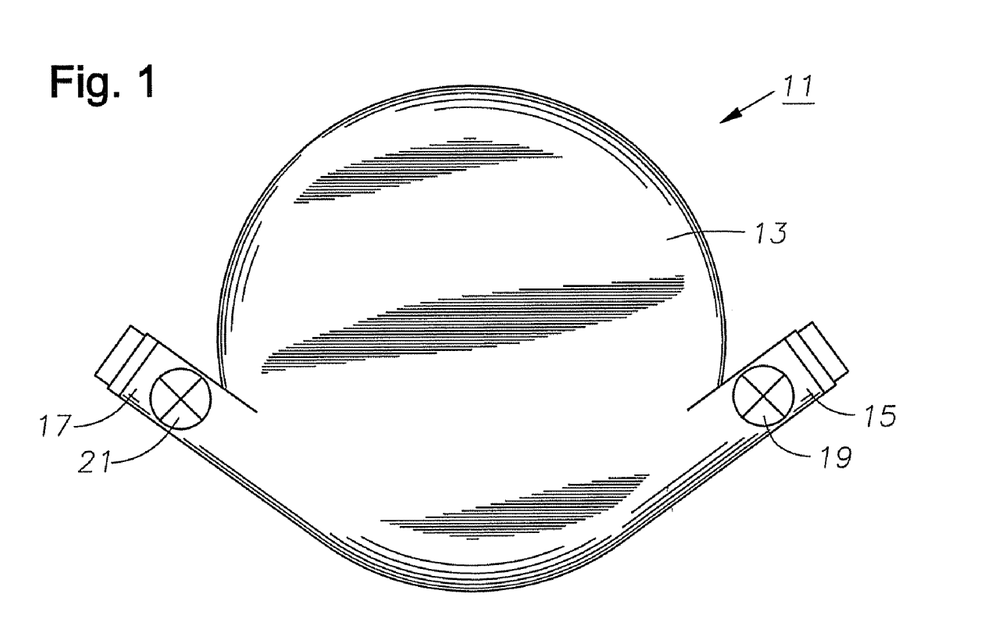
FIG. 1 is a front elevational view of a booster pump assembly constructed in accordance with this invention.

Referring to FIG. 1, the heart pump booster assembly includes a pump 11 that is of a stroking or reciprocating type. Pump 11 has a housing 13 with an inlet 15 and an outlet 17. Inlet 15 and outlet 17 are adapted to be connected to the heart or arteries in a human body when pump 11 is outside or implanted within. Inlet 15 and outlet 17 each have a check valve 19, 21 respectively that operate in reverse to each other.

Figure 3:
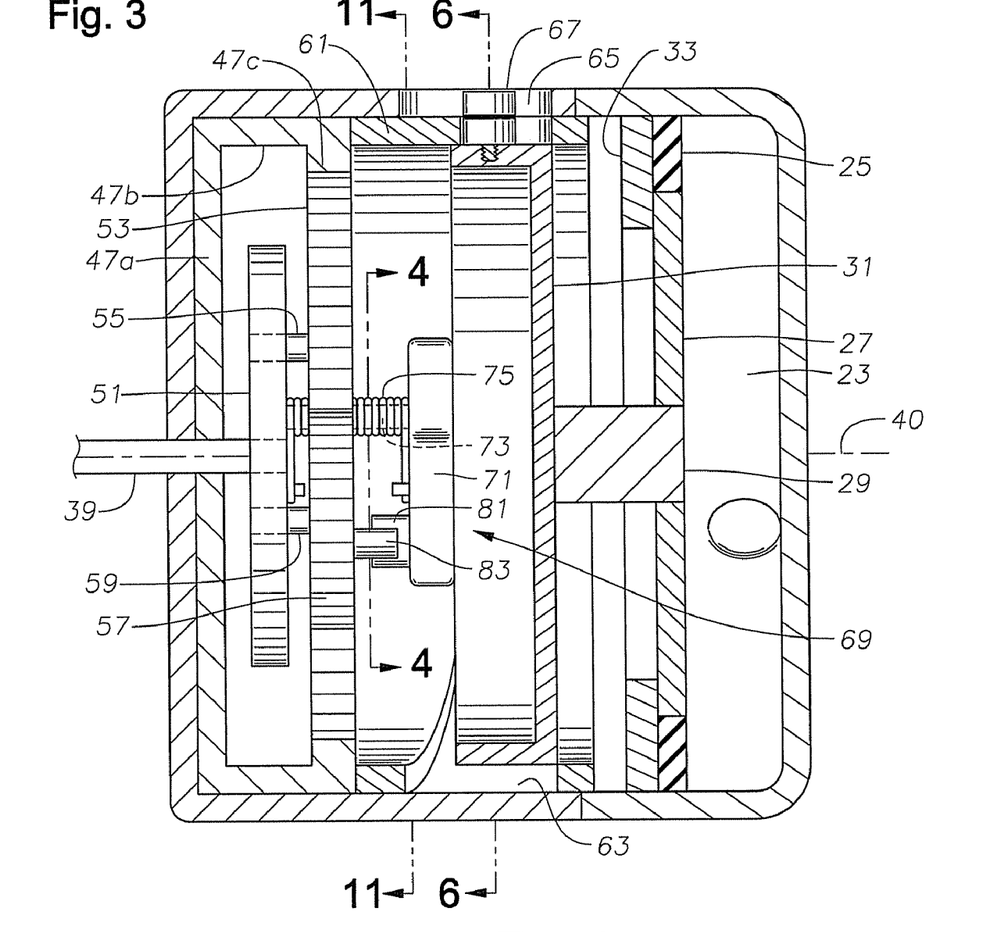
FIG. 3 is a sectional view of the booster pump assembly of FIG. 1.

Referring to FIG. 3, pump 11 has a chamber 23 within housing 13. A pump element or diaphragm 25 defines one side of chamber 23. In this embodiment, diaphragm 25 is an elastomeric annular member that has its outer diameter bonded or sealed to an interior portion of housing 13. A central plate 27, preferably metal, is bonded to the inner diameter of diaphragm 25 and forms a part thereof. A hub 29 extends rearwardly from central plate 27. Pump 11 could vary, such as having a piston rather than a flexible diaphragm.

An actuator cup 31 is mounted to the rearward end of hub 29 for moving hub 29 to the extended position. Cup 31 has a cylindrical outer wall and a flat base that mounts to hub 29 and may be considered to be part of the pump element assembly. A stop ring 33 is rigidly mounted in pump housing 13 to define the limit of the retracted and extended positions. When cup 31 is pushed forward, or to the right of the position shown in FIG. 3, diaphragm 25 will flex and central plate 27 will move forward to push blood contained within chamber 23 out check valve 21 and outlet 17 (FIG. 1). The resiliency of diaphragm 25 causes it to retract back toward the natural or retracted position shown in FIG. 3. When retracting, inlet check valve 19 opens to allow fluid to be drawn into inlet 15. When operated as a booster pump, the stroking is synchronized with the beat of the human's natural heart, such as by using a pacemaker, for boosting the pressure and flow rate of the blood flowing from the human heart.

Figure 2:
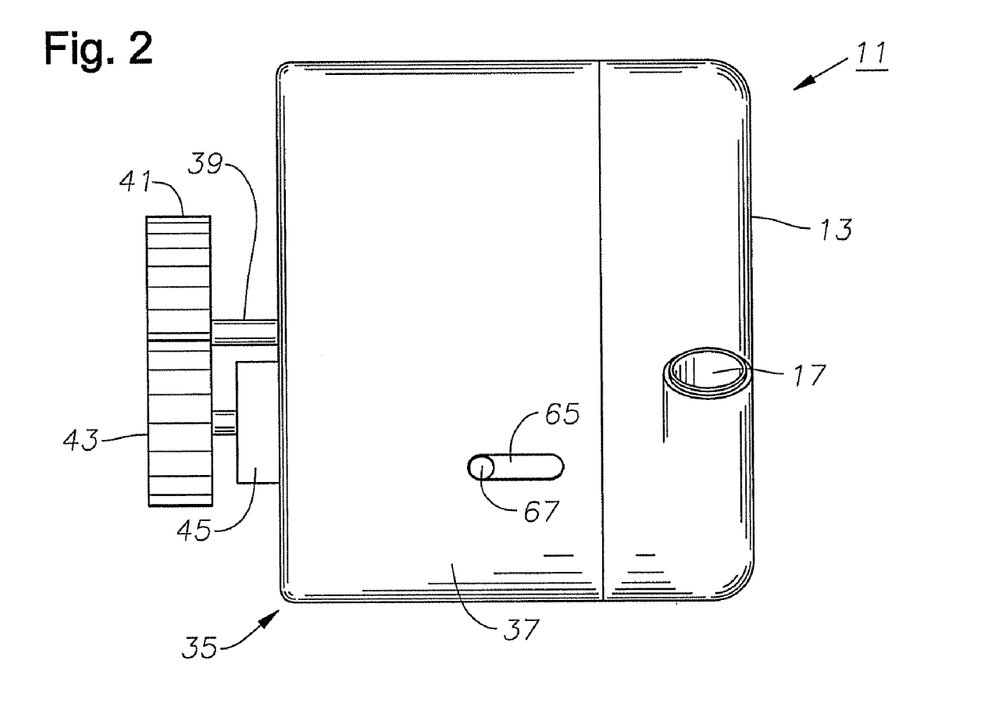
FIG. 2 is a side elevational view of the booster pump assembly of FIG. 1.

Referring to FIG. 2, a driver device 35 connects to pump 11 for driving pump 11. Driver 35 has a driver housing 37 that may be integral with or fastened to pump housing 13. A drive shaft 39 extends from the exterior through a hole in the rearward side of driver housing 37. Drive shaft 39 is located on a concentric axis 40 of driver housing 37. A driven gear 41 is mounted to shaft 39 for rotating it. A drive gear 43 engages driven gear 41 for rotating driven gear 41. Drive gear 43 is driven by a battery powered DC motor 45 that rotates continuously in one direction. Other gearing arrangements are feasible. In this embodiment, motor 45 rotates drive shaft 39 in only one direction.

Driver device 35 is incorporated with a reversing mechanism for converting rotary motion of drive shaft 39 to reciprocating movement of diaphragm 25. Referring to FIG. 3, drive shaft 39 extends rotatably through a back wall 47a of a ring gear 47, which forms part of the reversing mechanism in this embodiment. Ring gear 47 has a cylindrical wall 47b that is closely spaced to the inner diameter of driver housing 37. A plurality of teeth 47c are located on the inner diameter of ring gear cylindrical wall 47b. Ring gear 47 is rotatable relative to drive shaft 39 and driver housing 37.

A rotary disk 51 is rigidly mounted to drive shaft 39 within driver housing 37 for rotation with drive shaft 39. An outer gear 53 is rotatably mounted to the forward side of rotary disk 51 by a shaft or pin 55 spaced radially from axis 40. Outer gear 53 has teeth that engage ring gear teeth 47c. Preferably the number of ring gear teeth 47c is an even multiple of the teeth of outer gear 53, such as 2 to 1. If outer gear 53 rotates a full revolution while ring gear 47 is stationary, outer gear 53 will move around the full inner diameter of ring gear 47.

An inner gear 57 is also mounted to rotary disk 51 offset from main axis 40. Inner gear 57 is smaller in diameter than outer gear 53 and has fewer teeth. In this embodiment, inner gear 57 has one-third as many teeth that as ring gear 47. Inner gear 57 will rotate three full revolutions for each rotation around ring gear 47. Inner gear 57 engages the teeth of outer gear 53 and is mounted to rotary disk 51 by a pin 59.

A cylindrical cam ring 61 is rotatably carried within driver housing 37 forward of ring gear 47. Cam ring 61 has substantially the same outer and inner diameters as ring gear 47 in this embodiment. Cam ring 61 has a rearward edge that engages the forward edge of ring gear cylindrical wall 47b. Cam ring 61 is not rotatable relative to ring gear 47 and could be integrally formed with ring gear 47. Cam ring 61 and ring gear 47 are fixed in housing 37 against any axial movement along axis 40.

Figure 5:
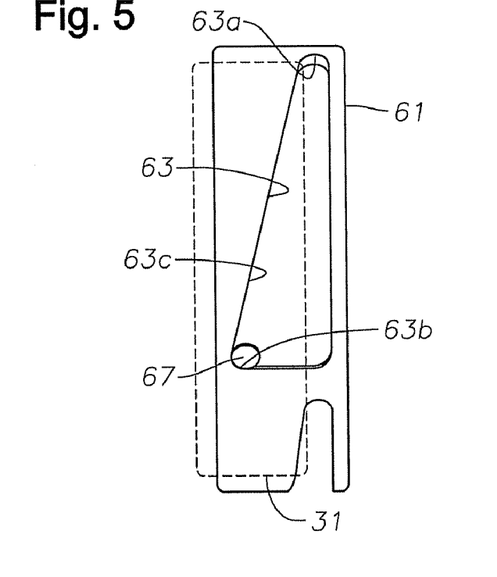
FIG. 5 is a side elevational view of a cam ring employed in the driver mechanism of the booster pump assembly shown in FIG. 3, shown removed from the housing and with dotted lines showing a portion of the pump in a retracted position.

As shown in FIG. 5, cam ring 61 has a cylindrical sidewall with a plurality of cam ring slots 63. In this embodiment, there are three slots 63, each extending approximately 120 degrees circumferentially, but the number and length could vary. Each cam ring slot 63 has a reduced width end that defines an extension end stop 63a. Each cam ring slot 63 enlarges gradually from extension end stop 63a to an enlarged width end that defines a retraction end stop 63b. In this embodiment, the forward edge of cam ring slot 63 is located in a plane perpendicular to axis 40 (FIG. 3) while the rearward edge 63 is located in an inclined plane, providing a triangular shape to cam ring slot 63.

Driver housing 37 has three elongated housing slots 65, although only one is shown in FIGS. 2, 3, 7 and 10. Each housing slot 65 is elongated in a direction parallel with axis 40. Each housing slot 65 extends axially approximately the same width as the width of cam ring retraction end stop 63b (FIG. 5). Each housing slot 65 is spaced approximately 120 degrees apart from the other. Although housing slots 65 as shown, extend through the wall of housing 37, they are not required to do so.

Figure 6:
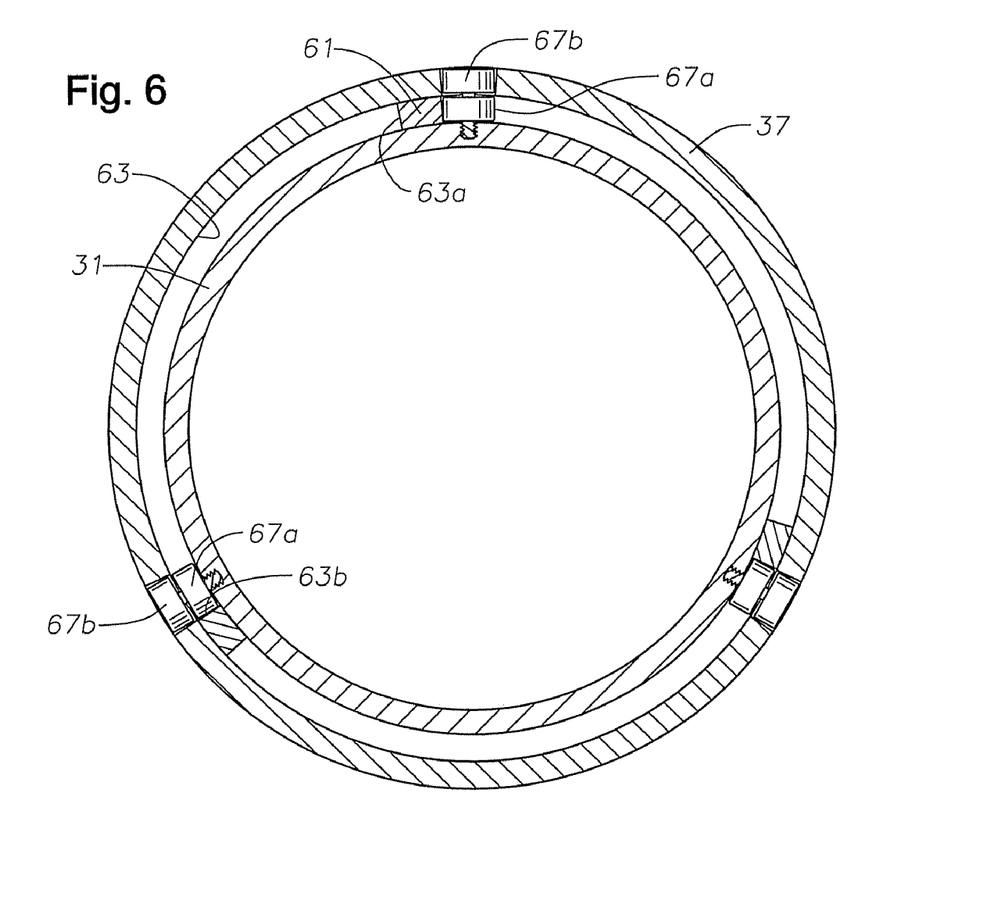
FIG. 6 is a sectional view of the booster pump assembly of FIG. 1, taken along the line 6-6 of FIG. 3, and showing cam ring in a retracted position.
Figure 7:
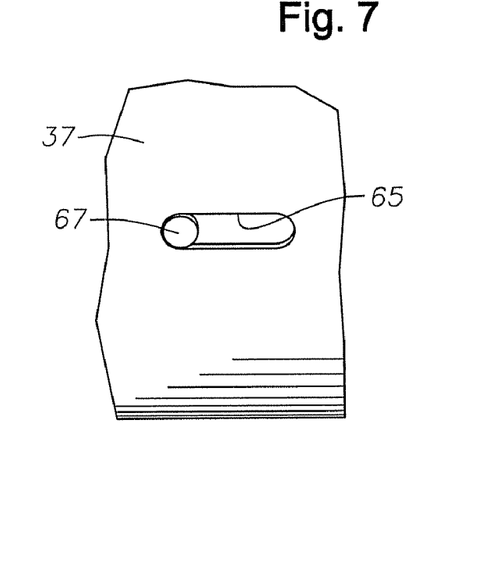
FIG. 7 is an enlarged elevational view of a portion of the housing of the booster pump assembly of FIG. 1, with the cam follower in a retracted position.

Three cam followers 67 are mounted to actuator cup 31 with threaded stems, as shown in FIG. 6. Each cam follower 67 has an inner roller 67a that rolls along and engages the edges of one of the cam ring slots 63. Each cam follower 67 has an outer roller 67b that rotatably engages the edges of one of the housing slots 65 (FIG. 2). In this embodiment, inner and outer rollers 67a, 67b can rotate relative to each other. Cam followers 67 are also spaced 120 degrees apart from each other.

When cam ring 61 rotates 120 degrees counterclockwise from the fully retracted position (FIG. 5) to the extended position (FIG. 8), each cam follower 67 will be forced by rearward edge 63c of cam ring slot 63 from retraction end stop 63b to the extension end stop 63a. Because the extension end stop 63a is more forward than retraction end stop 63b, cam followers 67 move axially forward. The forward movement of cam followers 67 advances actuator cup 31 in a forward direction as shown by the dotted lines in FIG. 8, which in turn pushes diaphragm 25 and central plate 27 forward from the position shown in FIG. 3.

Figure 4:
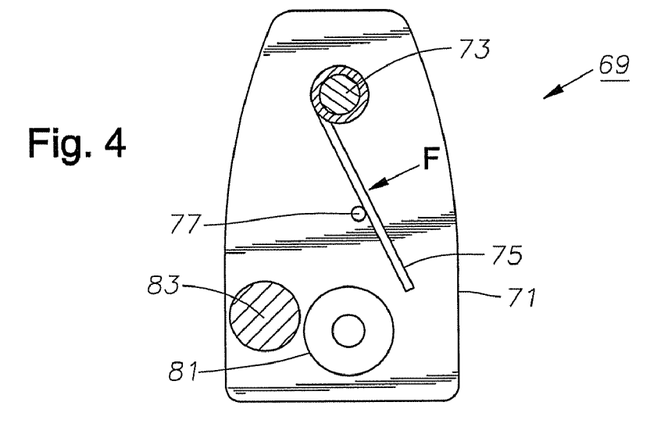
FIG. 4 is a sectional view of a stroke control device of the booster pump assembly of FIG. 1, taken along the line 4-4 of FIG. 3.

A stroke control device 69 allows the volume of flow of each stroke to change in response to the blood pressure or demand by the patient. Stroke control device 69 is a mechanical device that includes a support plate 71 mounted to rotary disk 51 forward of gears 53, 57. Support plate 71 is mounted by a single post 73 to rotary disk 51 and is rotatable relative to rotary disk 51. Post 73 is offset from central axis 40 and supports support plate 71 in cantilever fashion. A torsion spring 75 wraps around post 73 and has a leg portion that extends outward and engages a stop pin 77 (FIG. 4) mounted in support plate 71. Torsion spring 75 has an opposite leg (not shown) fixed to rotary disk 51. Torsion spring 75 is wrapped so that it exerts a force F, as shown in FIG. 4, urging support plate 71 to rotate around post 73 relative to rotary disk 51 (FIG. 3).

Support plate 71 is limited from rotating relative to rotary disk 51 by reason of a support plate roller 81 bearing against an inner gear pin 83. Support plate roller 81 is rotatably mounted to the rearward side of support plate 71 in an over center arrangement. Inner gear pin 83 is mounted rigidly to the forward side of inner gear 57 for rotation therewith. Inner gear pin 83 protrudes forwardly a short distance from inner gear 57 and is located on the pitch diameter or periphery of inner gear 57 in this embodiment. Inner gear pin 83 will rotate with inner gear 57 but will not orbit around support plate roller 81. The radius of the orbital travel of inner gear pin 83 while rotating in unison with gear 57 is less than the pitch diameter of support plate roller 81, thus keeping roller 81 always to one side of pin 83. As inner gear pin 83 moves clockwise against support plate roller 81 up to the point shown in FIG. 13, it will more tightly wind torsion spring 75. As viewed in FIG. 4, support plate 71 will pivot counterclockwise about 30 to 40 degrees during the extension stroke of diaphragm 25 (FIG. 3) because of pin 83 pushing against roller 81. When inner gear pin 83 reaches the orbital position slightly past that shown in FIG. 13, inner gear pin 83 no long obstructs support plate roller 81, causing the force F from torsion spring 73 to rapidly spin inner gear 57 in the same direction. That rotation causes ring gear 47 to rotate in the opposite direction, allowing diaphragm 25 to retract. Torsion spring 75 unwinds and support plate 71 pivots back to the position shown in FIG. 4. This cycle occurs three times for each revolution of outer gear 53 around the inner diameter of ring gear 47.

Figure 8:
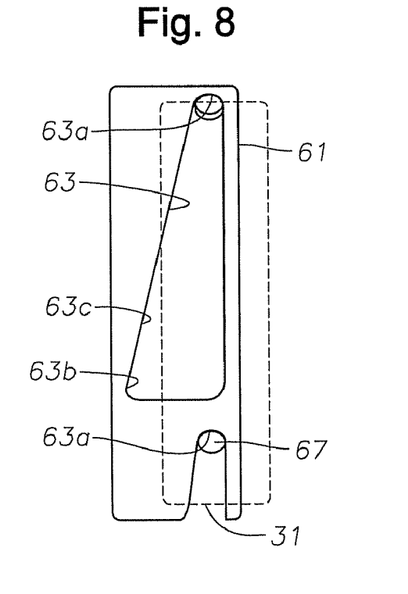
FIG. 8 is a side elevational view of the cam ring as shown in FIG. 5, but in an extended position.

In operation, motor 45 (FIG. 2) rotates drive shaft 39 continuously in one direction. Initially, drive shaft 39 will cause ring gear 47 and cam ring 61 to rotate. Cam followers 67 do not rotate with cam ring 61, thus each cam follower 67 will be forced by rearward edge 63c of cam ring slot 63 from retraction end stop 63b (as shown in FIG. 5) toward extension end stop 63a, which is about 120 degrees circumferentially from the initial position (as shown in FIG. 8). Because the extension end stop 63a is more forward than retraction end stop 63b, cam followers 67 move axially forward as can been seen by comparing FIGS. 5 and 8. The forward movement of cam followers 67 advances actuator cup 31 in a forward direction as shown by the dotted lines in FIG. 8, which in turn pushes diaphragm 25 and central plate 27 forward from the retracted position shown in FIG. 3.

Figure 9:
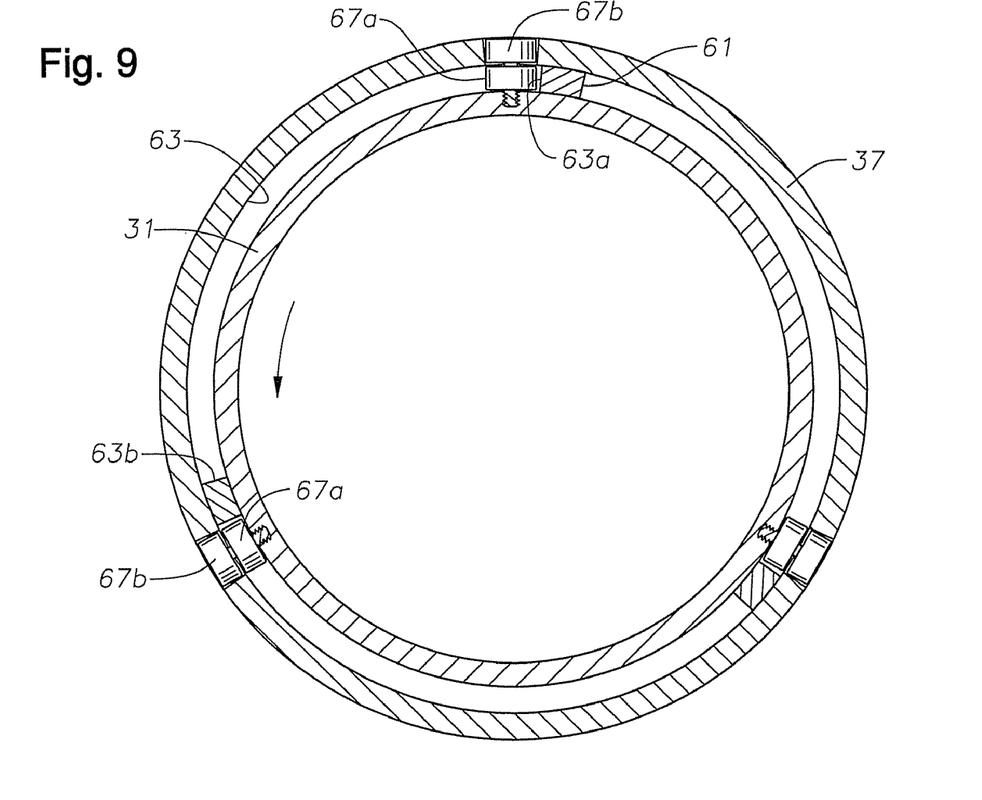
FIG. 9 is a sectional view similar to FIG. 6, but showing the cam ring in the extended position.
Figure 10:
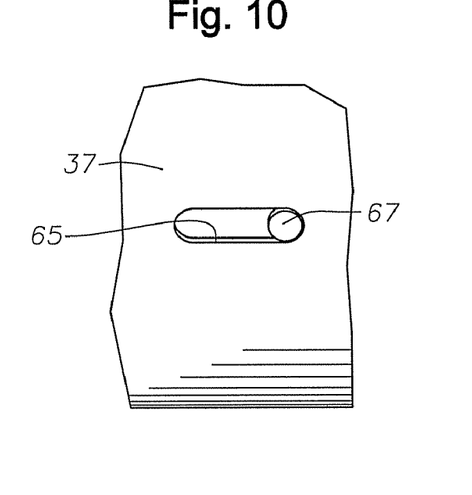
FIG. 10 is a side elevational view similar to FIG. 7, but showing the cam follower in the extended position.
Figure 11:
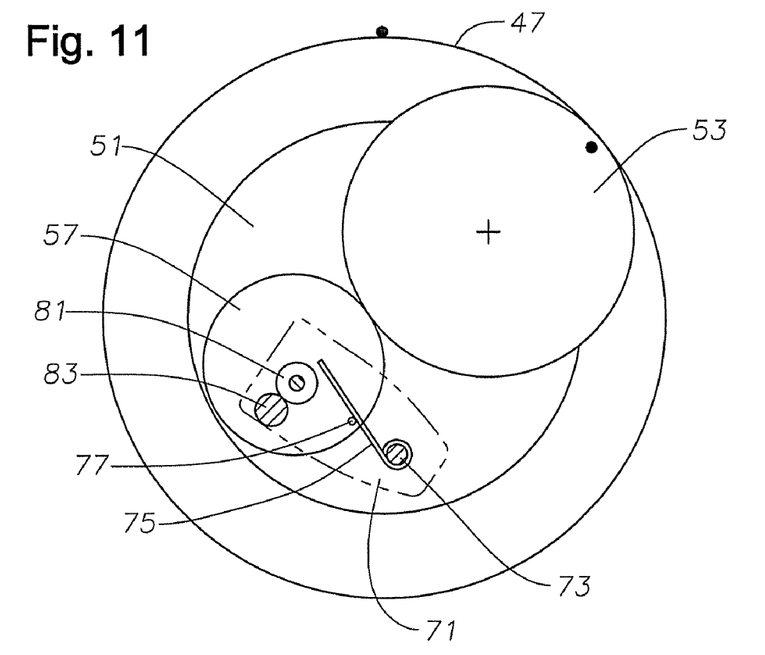
FIG. 11 is a schematic sectional view of the pump assembly of FIG. 1, taken along the line 11-11 of FIG. 3 and showing the driver in a retracted position.
Figure 12:
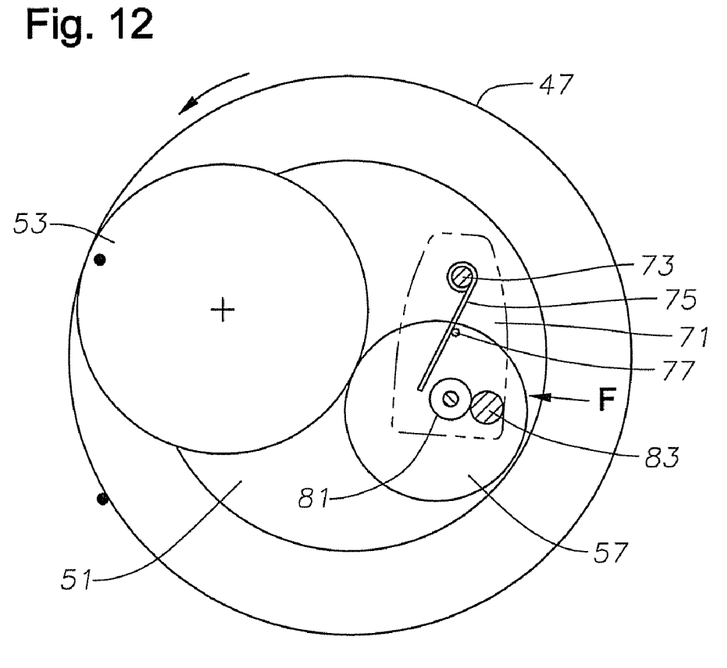
FIG. 12 is a sectional view similar to FIG. 11, but showing the ring gear of the driver and the stoke return device rotated in unison 120 degrees counterclockwise from that shown in FIG. 11 to an extended position.

FIG. 11 illustrates one example of the position of outer and inner gears 53, 57 while diaphragm 25 (FIG. 3) is in the retracted position, although this position can be adjusted to other orientations. Referring also to FIG. 3, the rotation of drive shaft 39 causes rotary disk 51 to rotate, which will also cause ring gear 47 to rotate in unison. As mentioned above, ring gear 47 initially rotates with rotary disk 51 because it is initially freely rotatable within driver housing 37. FIG. 12 shows the entire assembly of FIG. 11 rotated counterclockwise approximately 120 degrees. At this point, ring gear 47 and cam ring 61 cannot rotate any longer relative to housing 37 because of the engagement of cam followers 67 with extension end stops 63a and the forward ends of housing slots 65, shown in FIGS. 8-10. Motor 45 (FIG. 2) continues to rotate drive shaft 39 in the same direction without interruption when ring gear 47 and cam ring 61 stop rotating.

During the 120 counterclockwise rotation that causes diaphragm 25 (FIG. 3) to stroke forward in a power or pressure stroke, gears 53 and 57 rotate with ring gear 47 at a progressively increasing rate as the pressure in chamber 23 increases. Gears 53, 57 also rotate relative to each other and ring gear 47 during the extension stroke, but at a progressively decreasing rate as the force due to torsion spring 75 (FIG. 4) approaches the pressure in chamber 23. When the pressure in chamber 23 creates a force equal to the force created by torsion spring 75, gears 53, 57 rapidly rotate in the same direction while ring gear 47 reverses and rotates rapidly in the opposite direction. This places cam slot 73 in position for the next extension stroke. At the end of the 120 degree rotation of ring gear 47, the continued counterclockwise rotation of drive shaft 39 causes outer gear 53 to begin to rotate clockwise relative to ring gear 47, from the position in FIG. 12 to the position in FIG. 13. This rotation is relative to rotary disk 51 (FIG. 3), which is continuing to rotate counterclockwise with drive shaft 39 (FIG. 3), and also relative to ring gear 47, which is momentarily stationary.

Figure 13:
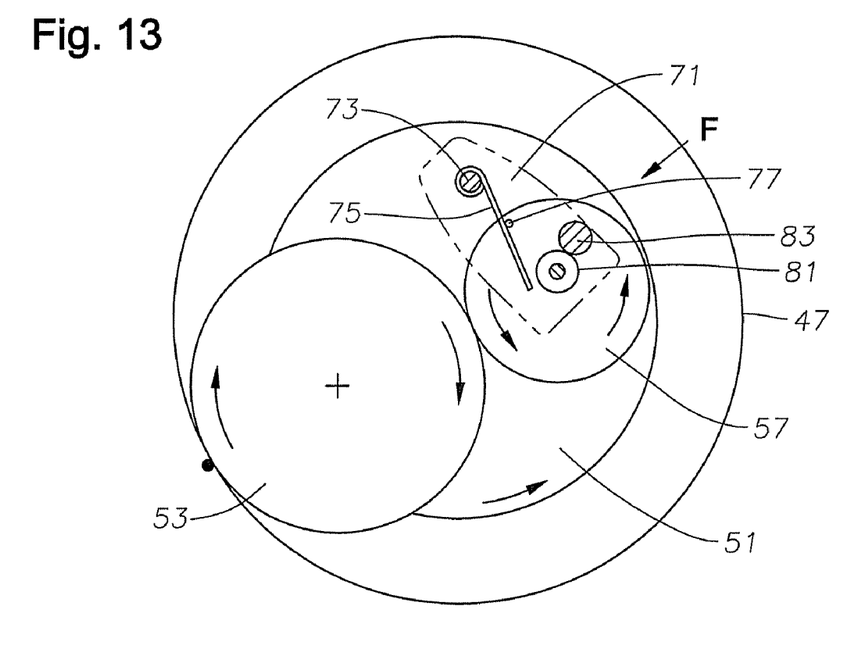
FIG. 13 is a sectional view similar to FIG. 12, but showing the stroke control device rotated approximately 120 degrees counterclockwise from the position shown in FIG. 12 while the ring gear remains stationary, just before the retraction movement of the ring gear begins.
Figure 14:
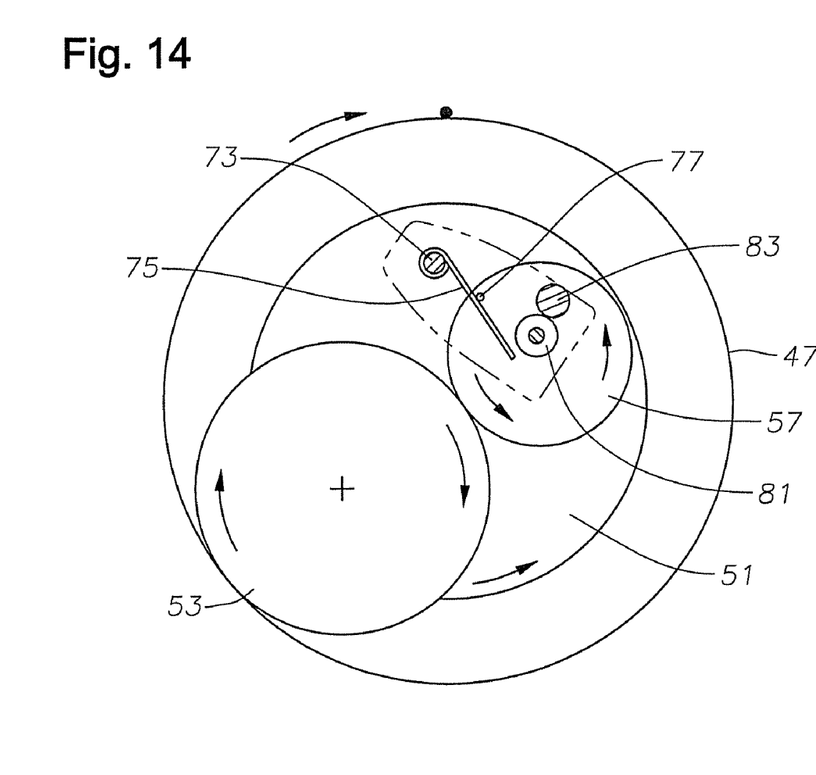
FIG. 14 is a sectional view similar to FIG. 13, but showing the ring gear rotated 120 degrees counterclockwise from the position shown in FIG. 13 back to the retracted position while the stroke return device remains stationary.

The rotation of outer gear 53 causes inner gear 57 to rotate counterclockwise (viewed from the FIG. 12 position), which in turn causes inner gear pin 83 to orbit counterclockwise against support plate roller 81 from the position in FIG. 12 to the position in FIG. 13. As inner gear 57 rotates, it will more tightly wind torsion spring 75 because the inner gear pin 83 causes support plate 71 to begin to rotate around post 73. Once inner gear pin 83 clears the over center arrangement with roller 75, which is slightly past the position shown in FIG. 13, inner gear pin 83 is no longer obstructed by the progressively increasing force of torsion spring 75. Then, the progressively decreasing force in torsion spring 75 will rapidly pivot support plate 71 about post 73 and rapidly propel inner gear 57 in a counterclockwise direction, as indicated in FIG. 14. This movement rapidly rotates outer gear 53 in the clockwise direction and ring gear 47 in the counterclockwise direction, as shown in FIG. 14. The clockwise rotation of ring gear 47 during the retraction stroke is much faster than the counterclockwise rotation of ring gear 47 during the extension stroke.

As ring gear 47 rotates quickly back toward the initial position shown in FIG. 11, cam ring 61 also rotates with ring gear 47 until its cam slot retraction ends 63b contact cam followers 67. During the retraction stroke, the pressure in chamber 23 (FIG. 3) and the resiliency of diaphragm 25 cause central plate 27 to move back to the retracted position shown in FIG. 3.

For a maximum power stroke and suction stroke, cam ring 61 will rotate 120 degrees counterclockwise with each extension of diaphragm 25 and 120 degrees clockwise with each retraction of diaphragm 25. The contact of extension end stops 63a with cam followers 67 cause the reversing mechanism to move to the retraction mode if the extension stroke is full. The contact of the retraction end stops 63b with cam followers 67 cause the reversing mechanism to move back to the extension mode. If the back pressure at pump inlet 15 was high during the retraction stroke and the back pressure at pump outlet 17 was low, the power and suction strokes might both extend the maximum amounts to stroke a maximum amount of blood with each stroke. The power and suction strokes would occur uniformly every 120 degrees of rotation of cam ring 61 as long as drive shaft 39 (FIG. 3) is rotated at a constant speed. For a maximum power stroke, diaphragm 25 would be fully extended when the end of the extension stroke is reached because cam slot extension end stop 63a (FIG. 5) would engage cam followers 67 before the retraction stroke starts and because the widths of retraction end stops 63a are only slightly greater than the widths of cam followers 67.

However, the back pressure at inlet 15 and outlet 17 are not always as mentioned above because the patient may be engaged in different types of activity. Stroke control device 69 automatically adjusts the length of both the suction stroke and the power stroke based on the back pressures at pump inlet 15 and outlet 17. Diaphragm 25 might not always be in the fully retracted position at the beginning of the power or extension stroke. Cam slot retraction end stops 63b are several times larger than the diameters of cam followers 67a. Because cam slots 63 are triangular openings, cam followers 67 are not required to engage the entire extent of cam slot rearward edges 63c during each stroke from extension end stop 63a to retraction end stop 63b. Cam ring 61 may start rotating back counterclockwise (viewed from the FIG. 6 position) for the extension stroke when cam follower 67 is engaging retraction end stop 63b but only half way to rearward edge 63c. Cam followers 67 will not start to stroke forward until contacted by retraction end stops 63b, but that contact might occur when diaphragm 25 has moved only half of the distance back to its fully retracted position. If so, the stroke length would be less, and the volume of blood less on the next extension stroke.

As mentioned, the pressure in chamber 23 can reduce the lengths of extension and retraction strokes from the maximum stroke lengths. The reversing mechanism comprising cam ring 61, ring gear 47 and outer gear 53, and cam followers 67 require an increase in torque to occur before shifting cam ring 61 to change its direction of rotation. On the retraction stroke, the increase in torque occurs only when retraction end stops 63b hit cam followers 67. The speed of rotation of cam ring 61 in the retraction direction is based on the force imposed by torsional spring 75 (FIG. 11) and does not depend upon the blood pressure in chamber 23. The speed of rotation in the retraction direction is much faster than the speed of rotation in the extension direction. Diaphragm 25 moves in the retraction direction in response to its own resilience as well as the force imposed by the pressure in chamber 23. During exercise, due to the larger volume of flow, the incoming blood flow into chamber 23 while diaphragm 25 is retracting creates a higher pressure that will tend to push it more quickly toward the fully retracted position. Consequently, cam followers 67 may move rearwardly so quickly so that cam retraction end stops 63b engage cam followers 67 only after or about the same time diaphragm 25 is fully retracted. When the extension stroke begins, cam followers 67 would be at the end of cam slot edge 63c farthest from diaphragm 25. If cam ring 61 didn't stop its extension rotation before reaching extension end stop 63a, a full incremental volume of blood would thus be pumped out of pump 11 on the next stroke.

On the other hand, if the blood circulation flow rate is low, such as when the patient is resting, the low rate of flow into chamber 23 creates a low pressure that would not push diaphragm 25 (FIG. 3) quickly enough for cam followers 67 to contact cam slot rearward edges 63c while at or near cam slot ends 63b. FIGS. 5 and 8 illustrate a full stroke along cam slot rearward edge 63c from end 63a to end 63b. If the patient was resting, the extension stroke might begin when diaphragm 25 has retracted only half its full distance. The volume of blood pumped would be proportionally lower in that instance. Rotating cam ring 61 during the retraction stroke much more quickly than during the power stroke and making the cam slot 63 triangular in shape allows the retraction stroke length to vary in response to the pressure exerted by the human heart.

If the blood pressure during the extension stroke is sufficiently high, such as when the patient is at rest, the pressure in chamber 23 during the extension stroke would create enough torque resistance to cause the extension stroke of diaphragm 25 to end before cam slot extension end stops 63a reach cam followers 67. The resistance to the forward movement of diaphragm 25 created by the high blood pressure in chamber 23 causes stroke controller 69 to move to its release position, releasing the force F of torsional spring 75. Once the torsional spring 75 force F is released, cam ring 61 ceases its forward stroke or counterclockwise movement (FIG. 6 to FIG. 7) and quickly moves clockwise toward the retracted position (FIG. 6). The clockwise movement (viewed from FIG. 6) stops the extension stroke and begins the retraction stroke. Stroke controller 69 can trigger this change in direction at any point along cam slots 63. For example, stroke controller 69 might trigger the end of the power stroke to occur at 80% the distance from cam slot end 63b to cam slot end 63a. Stroke controller 69 might cause the suction stroke to end at 60% the distance from cam slot end 63a to cam slot end 63b. The stroke in that instance would have a length proportional to 20% the distance between ends 63a and 63b.

In another embodiment, not shown, the various gears are eliminated. The cam comprises a rotary member with one or more inclined ramps or cam surfaces on its forward face. The ramps engages a mating ramps on a rearward side of a cam follower. The cam follower is connected to the pump element and prevented from rotating. As the cam surfaces on the cam slide on the ramps on the cam follower while the cam rotates in the first direction, the cam follower moves linearly in an extension direction. The cam surfaces have an extension end stop that stops rotation of the cam when the pump element is fully extended, and the reversing mechanism reverses the cam rotation to allow the pump element to retract in response to pressure in the chamber. The cam surfaces have a retraction end stop that stops rotation of the cam in the second direction at a fully retracted position and causes the reversing mechanism to shift the rotation back to the first direction.

As in the embodiment shown, the reversing mechanism of this second embodiment has a stroke controller portion that will vary the stroke length depending upon pressure in the chamber. In the second embodiment, the stroke controller has a hub that rotates continuously with the drive shaft. The reversing mechanism has a pivotal drive arm that is biased outward into engagement with an annular wall that surrounds it and is formed on the cam. The drive arm has a roller on its end that engages the annular wall to rotate the annular wall in unison with the shaft. When extension stop engages the cam follower, the roller begins to roll relative to the annular wall until it reaches the desired bias tension created by torsion and/or compression springs in the reversing mechanism. At that point another spring in the reversing mechanism causes the drive arm to flip over to an opposite orientation into engagement with another portion of the wall, which causes reverse rotation of the cam. If the torque is sufficiently high on the extension stroke, the drive arm will begin to roll relative to the cam earlier and flip over to the retraction stroke before reaching the fully extended position. Similarly if pressure is low in the chamber during the retraction, the pivotal arm may reach the recess and flip over to the extension stroke before the pump element has reached its fully retracted position.

The invention has significant advantages. The pump mechanically adjusts its stroke length in response to the pressure in the chamber. It thus will pump a greater volume with each stroke while the pressure is low, such as when the patient is exercising. While sedentary, the pump volume per stroke will decrease because the blood pressure increases. This ability makes the pump inherently more reliable than if it were required to pump the same volume regardless of blood pressure. Also, the heart pump more naturally duplicates a human heart than one that pumps the same volume of blood per stroke regardless of the patient's blood pressure. Electronic circuitry to attempt to control the pump in response to blood pressure is not required, thereby increasing the reliability of the device.

While the invention has been described in only a few of its forms, it should be apparent to those skilled in the art that it is not so limited, but is susceptible to various changes without departing from the scope of the invention. For example, although shown with a torsional spring, other arrangements may be employed to cause the cam ring to rotate back to the retracted position more quickly than its rotation to the extended position, such as a compression spring used. In addition, although the motor is shown as a constant speed motor, if desired, it could be of a variable speed type, with a variable speed pacemaker causing different rotational speeds. In addition, although the use described is for a heart pump, the pump could be used for other purposes where a stroke rate that varies according to the back pressure is desired.

The invention claimed is:

1. A pump, comprising:
a housing having a pump chamber with an inlet and an outlet for connection to suction and discharge conduits;
a pump element in the pump chamber that strokes between a retracted and an extended position to pump fluid from the chamber;
a motor mounted to the housing, the motor rotating a drive shaft;
a reversing mechanism coupled between the drive shaft of the motor and the pump element for converting rotary motion of the drive shaft to reciprocal stroking movement of the pump element while the drive shaft continues to rotate in the same direction;
the reversing mechanism having a mechanical stroke length controller for varying a stroke length of the pump element in response to changes in fluid pressure in the pump chamber;
a cam that rotates relative to the housing an increment of one turn in a first direction while the reversing mechanism is in an extension mode and an increment of one turn in a second direction while the reversing mechanism is in a retraction mode; and
a cam follower in engagement with the cam and being axially movable in unison with the pump element along an axis of the pump element, the cam pushing the cam follower and the pump element toward the extended position while the reversing mechanism is in the extension mode.

2. The pump according to claim 1, wherein:
the rate at which the pump element moves toward the retracted position varies depending upon the fluid pressure within the chamber.

3. The pump according to claim 1, wherein:
the stroke length controller comprises:
a spring assembly that biases the reversing mechanism into an extension mode, and if the fluid pressure in the chamber exceeds the bias force created by the spring assembly, the stroke controller causes the reversing mechanism to shift to a retraction mode.

4. The pump according to claim 3, wherein the stroke length controller causes the retraction mode to occur more quickly than the extension mode.

5. The pump according to claim 1, wherein:
the cam has an extension end stop that engages the cam follower to stop rotation of the cam when the pump element is at a fully extended position and a retraction end stop that engages the cam follower stops rotation of the cam when the pump element is at a fully retracted position; and
the reversing mechanism shifts to rotate the earn in an opposite direction when each of the end stops engages the cam follower.

6. The pump according to claim 5, wherein while the fluid pressure in the chamber is above a selected level and the reversing mechanism in the extension mode, the stroke length controller will cause the reversing mechanism to rotate the cam in the second direction prior to the extension end stop engaging the cam follower.

7. The pump according to claim 6, wherein while the fluid pressure in the chamber is below a selected level and the reversing mechanism in the refraction mode, the stroke length controller will cause the reversing mechanism to rotate the cam in the first direction prior to the pump element reaching a fully retracted position.

8. A pump for pumping blood for a patient, comprising:
a housing having a pump chamber with a longitudinal axis and an inlet and an outlet for fluid communication with arteries of the patient;
a pump element in the pump chamber that strokes along the axis between a retracted and an extended position to draw blood into the chamber and pump blood from the chamber;
a motor mounted to the housing, the motor rotating a drive shaft;
a cam rotatably mounted in the housing;
a reversing mechanism coupled between the drive shaft of the motor and the cam for rotating the cam an increment less than one turn in a first direction, then rotating the cam an increment less than one turn in a second direction while the motor continues to rotate the drive shaft in the same direction; and
a cam follower operatively coupled to the pump element for axial movement and in engagement with the cam for pushing the pump element toward the extended position when the cam is rotating in the first direction, and for causing the pump element to move toward the retracted position while the cam is rotating in the second direction.

9. The pump according to claim 8, wherein the reversing mechanism has a mechanical stroke length controller that varies a stroke length of the pump element in response to changes in blood pressure in the pump chamber.

10. The pump according to claim 8, wherein while the cam is rotating in the second direction, the pump element moves toward the retracted position at a rate depending upon blood pressure in the chamber.

11. The pump according to claim 8, further comprising:
the cam has an extension end stop that engages the cam follower to stop rotation of the cam when the pump element is at a fully extended position and a retraction end stop that engages the cam follower stops rotation of the cam when the pump element is at a fully retracted position; and
the reversing mechanism shifts to rotate the cam in an opposite direction when each of the end stops engages the cam follower.

12. The pump according to claim 11, wherein while the blood pressure in the chamber is above a selected level and the reversing mechanism in the extension mode, the stroke length controller will cause the reversing mechanism to rotate the cam in the second direction prior to the extension end stop engaging the cam follower.

13. The pump according to claim 8, wherein while the blood pressure in the chamber is above a selected level and the reversing mechanism in the extension mode, the stroke length controller will cause the reversing mechanism to rotate the cam in the second direction prior to the pump element reaching a fully extended position.

14. The pump according to claim 8, wherein while the blood pressure in the chamber is below a selected level and the reversing mechanism in the retraction mode, the stroke length controller will cause the reversing mechanism to rotate the cam in the first direction prior to the pump element reaches the full retraction stroke.

15. A pump for pumping blood for a patient, comprising:
   a housing having a pump chamber with an inlet and an outlet for fluid communication with arteries of the patient;
   a pump element in the pump chamber that has a fully retracted position and a fully extended position;
   a motor mounted to the housing, the motor rotating a drive shaft;
   a cam rotatably mounted in the housing and having a retraction end stop and an extension end stop spaced circumferentially from the retraction end stop;
   a cam follower operatively connected to the pump element for axial movement in unison with the pump element and restricted from rotary movement relative to the housing, the cam follower being in engagement with the cam for moving linearly as the cam rotates to cause the pump element to move linearly;
   a reversing mechanism coupled between the drive shaft of the motor and the cam having a full extension stroke mode wherein the drive shaft rotates the cam in a first direction until the extension end stop engages the cam follower, which exerts an end-of-stroke force that causes the cam to rotate in a second direction until the retraction end stop engages the cam follower, which in turn exerts an end-of-stroke force that causes the cam to again rotate in the first direction; and the reversing mechanism having a spring assembly that biases the reversing mechanism such that if a reactive force due to blood pressure in the chamber becomes sufficiently high while
   the cam is moving in the first direction, the reactive force will cause the cam to rotate in the second direction before the extension end stop engages the cam follower and before the pump element reaches the fully extended position.

16. The pump according to claim 15, wherein the pump element has a resilient member that applies a resilient force to urge the pump element toward the retracted position while the pump element is moving toward the extended position, and when the cam is rotating in the second direction, the resilient force and the reactive force cause the pump element to move toward the retracted position.

17. The pump according to claim 16, wherein:
   the spring assembly causes the cam to rotate in the second direction more rapidly than the motor rotates the cam in the first direction, so that if the reactive force due to blood pressure in the chamber is sufficiently low, the reversing mechanism will cause the cam to reverse and rotate in the first direction before the pump element reaches the fully retracted position.

* * * * *